United States Patent
Watanabe

(10) Patent No.: US 6,433,870 B1
(45) Date of Patent: Aug. 13, 2002

(54) ROBOT SYSTEM FOR MEASURING DUST AND PARTICLES IN DUCT

(75) Inventor: Yasuo Watanabe, Musashmurayama (JP)

(73) Assignee: M. T. System Co. Ltd., Tokyo (JP)

( * ) Notice: Subject to any disclaimer, the term of this patent is extended or adjusted under 35 U.S.C. 154(b) by 0 days.

(21) Appl. No.: 09/468,096

(22) Filed: Dec. 21, 1999

(30) Foreign Application Priority Data

Sep. 20, 1999 (JP) .............................. 11-266129

(51) Int. Cl.[7] .................... G01N 21/00; A47L 15/00
(52) U.S. Cl. .................. 356/337; 356/336; 15/304; 15/319
(58) Field of Search ................ 356/337, 336–343; 315/304, 319

(56) References Cited

U.S. PATENT DOCUMENTS 4,420,256 A * 12/1983 Fladda et al. ............... 356/336
5,572,766 A * 11/1996 Matsuura et al. ............ 15/304
6,026,538 A * 2/2000 Watanabe .................... 15/304

* cited by examiner

Primary Examiner—Frank G. Font
Assistant Examiner—Layla Lauchman
(74) Attorney, Agent, or Firm—Armstrong, Westerman & Hattori, LLP

(57) ABSTRACT

The object of the present invention is to provide a dust measuring system, which can efficiently measure an amount of dust accumulated in a duct and can display the measured value at real time in a remote place. The system of the present invention comprises a running device moving in the duct by remote-controlled operation, being equipped with an accumulated dust separator, a dust concentration measuring unit and a video camera, means for measuring the dust separated and turned to loose state by said accumulated dust separator using said dust concentration measuring unit and for transmitting the measured data to a data processing unit, and a display unit for displaying an image including numerical values and graphs prepared by said data processing unit.

5 Claims, 2 Drawing Sheets

ROBOT SYSTEM FOR MEASURING DUST AND PARTICLES IN DUCT

BACKGROUND OF THE INVENTION

The present invention relates to a robot system for measuring dust and particles accumulated in a duct, which can indirectly measure the amount of accumulated dust and particles in a duct and can display the measured value at real time in a remote place.

In a duct installed in a building or other facilities, mold or bacteria are proliferated in dust accumulated in it (bacteria may be proliferated sometimes to about 100,000 bacteria per $m^3$). These bacteria or mold are blown out or diffused through outlet of the duct into rooms, and it is reported that this may cause hospital-acquired infection in hospitals or food poisoning at restaurants and the like.

The measurement of the accumulated dust and particles has not been performed in the past, nor any method for such measurement in the duct has been known.

The measurement of the amount of dust accumulated in the duct is very important in making decision as to when cleaning should be performed to clean up the inner space of the duct, or in identifying how far the accumulated dust has been cleaned up after duct cleaning.

However, if it is tried to measure the amount of the accumulated dust by setting an access point at each of the measuring points, working efficiency would be very low, and it is almost impossible to perform the measurement of the dust in such manner.

SUMMARY OF THE INVENTION

It is an object of the present invention to provide a system for measuring dust, by which it is possible to efficiently measure the amount of accumulated dust in a duct and to display the measured value at real time in a remote place.

To attain the above object, the system according to the present invention comprises a running device moving in the duct by remote-controlled operation, being equipped with an accumulated dust separator, a dust concentration measuring unit and a video camera, means for measuring the dust separated and turned to loose state by said accumulated dust separator using said dust concentration measuring unit and for transmitting the measured data to a data processing unit, and a display unit for displaying an image including numerical values and graphs prepared by said data processing unit.

In fact, the system of the present invention is designed in such manner that the dust accumulated in a duct is separated by an accumulated dust separator and is turned to loose state to float in the air, and the amount of the dust is determined by the dust concentration measuring unit. As a result, the amount of the accumulated dust is indirectly measured. Further, the measuring unit is placed on a running device so that it can be freely moved to any measuring point.

The above and other objects and advantages of the invention will become more apparent from the following description.

DETAILED DESCRIPTION OF THE PREFERRED EMBODIMENT

Description will be given below on an embodiment of the present invention referring to the attached drawings.

Figure 1:
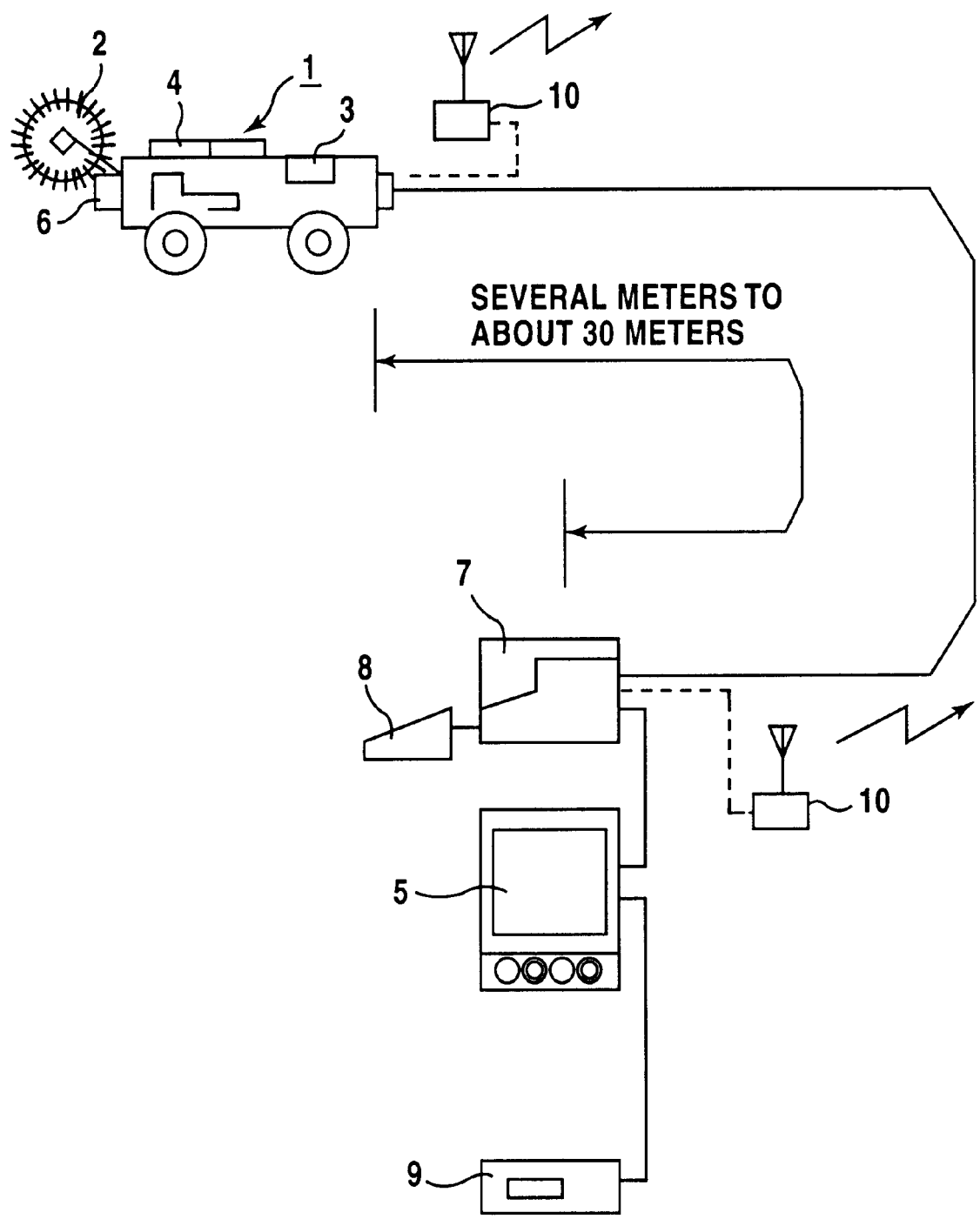
FIG. 1 is a block diagram of a system according to the present invention.

As shown in FIG. 1, an accumulated dust separator 2, a dust concentration measuring unit 3, and a video camera 4 are provided on a running device 1.

As the accumulated dust separator 2, a rotary brush, an air jet or a duster may be used. There is no special restriction on this dust separator as far as it can separate, peel off and turn the accumulated dust to loose state to float in the air. Adequate means should be selected according to the conditions of the accumulated dust. It is designed in such manner that the accumulated dust separator 2 is moved up when the device is running, while it is moved down to floor or wall of the duct when it is used to separate and peel off the dust.

As the dust concentration measuring unit 3, a measuring system of any known type may be used, which can measure the amount of dust by irradiating light beam to the dust and measuring the amount of transmitted light or by measuring the amount of scattered light. An adequate type of measuring unit should be selected depending on concentration and particle size of the dust.

The running device 1 is monitored according to an image taken by the video camera 4 and displayed on the display unit 5. By the control of a remote-controlled switch on an operation/display unit 8, it is moved to a site where measurement should be performed.

On the running device 1, an illuminating lamp 6 for assisting image-taking by the video camera 4 is arranged. The video camera 4 plays a role in such operation as image-taking of the site to be measured and monitoring of the surrounding conditions.

The present system is used to display the measured value at real time in a place away from the duct, in which the amount of dust is measured. The measurement data is transmitted from the measuring point to a place away from the measuring point (usually, several to 30 meters away).

The transmission may be in analog mode or in digital mode. Or, a cable interface may be used or a wireless transmitter/receiver may be used. The transmission itself may be performed by any known method. In order to prevent deterioration of signals in the transmission line, the analog type transmitter/receiver is designed to perform voltage/current conversion, voltage/pulse frequency conversion, etc.

In the digital type transmitter/receiver, the data is converted from digital data to serial data by A/D conversion.

The analog receiver is a circuit, which restores the signal converted by the transmitter such as current, pulse frequency, etc. to the original data.

The digital type receiver is used to restore the serial data converted by the transmitter to parallel data.

A cable driver/receiver may be used as the cable interface, and a wireless transmitter/receiver 10 (wireless TX/RX) such as RF-Optical may be used as the wireless transmitter/receiver.

A data processing unit 7 comprises a central processing unit (CPU) and an image synthesizer. Here, numeral data transmitted as described above is received, and processing such as range designation, parameter setting for input value vs. concentration conversion coefficient, range coefficient processing, averaging, integration processing, etc. are performed by the method of any known type. Then, display picture is prepared to display numerical data and graphs, and these are synthesized with the image taken by the camera.

The operation/display unit 8 operates the running device 1 and video camera and displays the image on the display unit 5.

In the running operation, the running device 1 is remotely controlled by the remote-control switch while the moving of the running device is monitored, using the video camera, on the image displayed on the display unit 5, and the running device 1 is moved in forward, backward, leftward, or rightward direction. Video camera control is to control camera operation such as zoom-in or zoom-out.

In picture display, the image of the camera or synthesized image including camera image and numerical value or graphic data is displayed on the display unit 5 using display devices such as CRT, LCD monitor, PDP, etc.

A recorder 9 comprises an image recorder and a printer.

The image recorder is an image media recorder such as VTR, DVD, etc., and the image displayed on the display unit is recorded. Because the measured values such as dust concentration (graph) are recorded as an image, a general type video recorder may be used, and expensive device for industrial use is not required.

As the printer, a printer comprising a printer board on a data processing unit and provided with printing software and capable to record graphs and numerical data on paper sheet may be used. Next, description will be given on a method to measure the amount of dust, which is accumulated in a duct where the system of the present invention is used.

The running device 1 is positioned at an access point in a duct, and the running device 1 is moved to a measuring position within the range of the video camera 4. Then, the rotary brush 2 is moved down to floor or wall of the duct, and accumulated dust is peeled off and set to loose state. Then, dust concentration is measured using the dust concentration measuring unit 3. The accumulated dust is separated using the rotary brush, and measurement is performed for 10 minutes while the dust is in loosed state and floating in the air.

The image taken by the video camera 4 and the value measured by the dust concentration measuring unit 3 are turned to a signal. This signal is transmitted by digital or analog transmission and is received at the data processing unit 7. An image synthesized from camera image and numerical value or graph prepared in the data processing unit 7 is displayed on the display unit 5, and this is stored in a storage device 9 such as video tape recorder.

Figure 2:
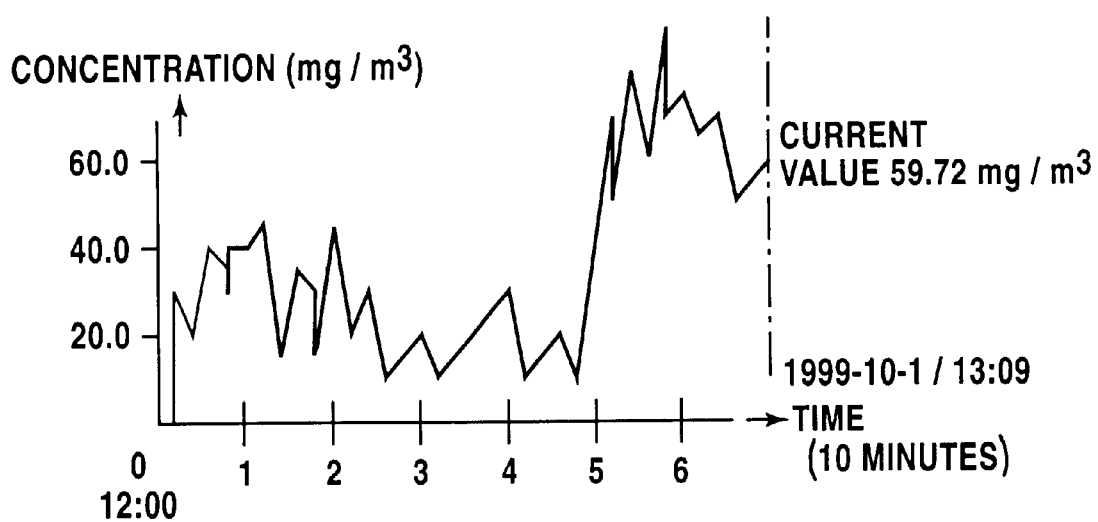
FIG. 2 is a graph showing dust concentration recorded by the system of the present invention.

FIG. 2 shows a graph prepared as described above. In the graph shown in FIG. 2, the measuring point where the current value has been obtained is to be shown. (In the figure, the image of the measuring point is not shown.) Therefore, the values of the dust amount at any desired point can be easily identified from the image stored on video. When measurement is performed without moving the running device 1, it is possible to determine the changes over time of dust concentration at that point.

According to the present invention, the measuring unit is arranged on the running device, and it is possible to easily and continuously measure the amount of dust at any desired point by moving the running device in the duct if a single access point is determined.

The system of the present invention can be used for such purposes as in making decision whether it is necessary or not to perform cleaning in the duct or in finding out how far the accumulated dust has been cleaned up after cleaning operation.

The system of the present invention may be used to perform cleaning operation in the duct. In such case, however, it is necessary to provide the means to discharge the floating dust out of the duct. In so doing, cleaning operation can be carried out while confirming whether the cleaning operation has been performed to full extent or not.

According to the present invention, the amount of dust accumulated in the duct which has been not easily identifiable in the past can be indirectly and easily measured. The system of the present invention is very useful for such purposes as in making decision whether it is necessary or not to perform cleaning in the duct or in finding out how far the accumulated dust has been cleaned up after cleaning operation.

I claim:

1. A robot system for measuring an amount of dust in a duct, comprising a running device moving in the duct by remote-controlled operation, being equipped with an accumulated dust separator, a dust concentration measuring unit and a video camera, means for measuring the dust separated and turned to loose state by said accumulated dust separator using said dust concentration measuring unit and for transmitting the measured data to a data processing unit, and a display unit for displaying an image including numerical values and graphs prepared by said data processing unit.

2. A system according to claim 1, wherein said running device operates a running unit by remote controlled operation while monitoring the running operation based on a signal from said video camera.

3. A system according to claim 2, wherein an image synthesized from the video camera image and numerical value or graph of the dust concentration prepared by said data processing unit is displayed on said display unit.

4. A system according to claim 1, wherein said accumulated dust separator is a rotary brush, an air jet, or a duster.

5. A system according to claim 1, wherein said dust concentration measuring unit is a measuring unit for measuring the dust by irradiating light beam to the dust and measuring an amount of transmitted light or by measuring an amount of scattered light.

* * * * *